United States Patent
Bhaidasna et al.

(10) Patent No.: US 9,398,640 B2
(45) Date of Patent: Jul. 19, 2016

(54) DIGITAL MULTI-USE THERMO-CUP

(71) Applicant: Halliburton Energy Services, Inc. ("HESI"), Duncan, OK (US)

(72) Inventors: Ketan C. Bhaidasna, Houston, TX (US); Christopher R. Bell, Humble, TX (US); Justin T. Loop, Friendswood, TX (US); Viatcheslav Tchernin, Spring, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 530 days.

(21) Appl. No.: 13/725,998

(22) Filed: Dec. 21, 2012

(65) Prior Publication Data

US 2014/0175083 A1 Jun. 26, 2014

(51) Int. Cl.
*H05B 1/02* (2006.01)
*G01N 25/02* (2006.01)
*G01N 25/04* (2006.01)
*G01N 33/28* (2006.01)
*G01N 25/00* (2006.01)
*G01N 25/48* (2006.01)

(52) U.S. Cl.
CPC ............ *H05B 1/0269* (2013.01); *G01N 25/02* (2013.01); *G01N 25/00* (2013.01); *G01N 25/04* (2013.01); *G01N 25/4826* (2013.01); *G01N 33/28* (2013.01)

(58) Field of Classification Search
None
See application file for complete search history.

(56) References Cited

U.S. PATENT DOCUMENTS

| | | | | |
|---|---|---|---|---|
| 2,856,489 A | * | 10/1958 | Bletz | 337/392 |
| 2,936,359 A | * | 5/1960 | Sheahan | 219/441 |
| 3,007,028 A | * | 10/1961 | Sorenson | 219/442 |
| 3,007,029 A | * | 10/1961 | Levine | 219/442 |
| 3,393,295 A | * | 7/1968 | Jepson et al. | 219/398 |
| 3,681,568 A | * | 8/1972 | Schaefer | 219/432 |
| 4,191,173 A | | 3/1980 | Dedeian et al. | |
| 4,256,697 A | * | 3/1981 | Baldwin | 422/562 |
| 4,342,234 A | | 8/1982 | Bernath | |
| 4,463,664 A | * | 8/1984 | Peace | 99/323.3 |
| 4,993,480 A | * | 2/1991 | Suzuki et al. | 165/254 |

(Continued)

FOREIGN PATENT DOCUMENTS

WO 2014/100500 6/2014

OTHER PUBLICATIONS

Ofite, Universal Heat Cup, Instructions, published no later than Dec. 2011.*

(Continued)

*Primary Examiner* — Joseph M Pelham
(74) *Attorney, Agent, or Firm* — Krueger Iselin LLP; Craig Roddy

(57) ABSTRACT

A multi-use thermal cup device is provided that includes a cup, a sensor, a thermometer, a user interface, and an electronic controller. The cup has at least one heating element disposed between its inner and outer walls. Electro-mechanical connection points are included on the outer wall of the cup and the electronic controller, which are sized to allow the controller to be connected to the cup at a distance sufficient to insulate the controller from heat dispersed from the cup. An insulating air gap is formed between the cup and the electronic controller to protect the controller from any dissipating heat. The controller is programmable to direct the power supply to the heat conductors and to control the function of any device connected to the sensor in response to information received from the sensor and the user-defined sampling parameters.

20 Claims, 4 Drawing Sheets

(56) References Cited

U.S. PATENT DOCUMENTS

| | | | |
|---|---|---|---|
| 5,019,690 A * | 5/1991 | Knepler | 219/400 |
| 5,477,029 A * | 12/1995 | Skutt et al. | 219/390 |
| 5,842,353 A * | 12/1998 | Kuo-Liang | 62/190 |
| 5,864,120 A * | 1/1999 | Vroom et al. | 219/400 |
| 6,313,446 B1 * | 11/2001 | Jones | 219/433 |
| 6,362,459 B1 * | 3/2002 | Schmidt | 219/414 |
| 6,674,052 B1 | 1/2004 | Luo | |
| 6,788,084 B2 | 9/2004 | Jones et al. | |
| 7,112,764 B2 * | 9/2006 | Garcia | 219/429 |
| 7,605,349 B2 * | 10/2009 | Gaynor et al. | 219/442 |
| 2002/0094581 A1 | 7/2002 | Cole | |
| 2008/0083730 A1 * | 4/2008 | Dolgov et al. | 219/432 |
| 2009/0008249 A1 | 1/2009 | Chou et al. | |
| 2009/0166350 A1 * | 7/2009 | Ho | 219/441 |
| 2010/0314379 A1 | 12/2010 | Lin | |
| 2011/0201127 A1 | 8/2011 | Feilders et al. | |
| 2011/0215081 A1 * | 9/2011 | Beer | 219/385 |
| 2011/0259871 A1 * | 10/2011 | Li | 219/441 |
| 2013/0008182 A1 * | 1/2013 | Hrudka | 62/3.6 |
| 2013/0240500 A1 * | 9/2013 | Alipour et al. | 219/438 |

OTHER PUBLICATIONS

OFI Testing Equipment, "Heat Cups and Thermocups", www.ofite.com/products.asp?category=Thermocups, (Date Unknown), 2 pgs.

Fann Instrument Company, "Model 35 Viscometer Accessories", (2007), 3 pgs.

PCT International Search Report and Written Opinion, dated Jun. 26, 2014, Appl No. PCT/US2013/076836, "Digital Multi-Use Thermo-Cup," Filed Dec. 20, 2013, 14 pgs.

PCT International Preliminary Report on Patentability, dated Jul. 2, 2015, Appl No. PCT/US2013/076836, "Digital Multi-Use Thermo-Cup," Filed Dec. 20, 2013, 10 pgs.

* cited by examiner

DIGITAL MULTI-USE THERMO-CUP

BACKGROUND

In many fields, it is necessary to heat materials to determine certain characteristics (e.g., melting point, boiling point, viscosity as a function of temperature, etc.) or even to create new materials. It is often desirable to perform such analyses (at least initially) on a small scale, thereby limiting the amount of material and effort involved in the analysis.

Accordingly, industry has developed "thermo-cups", also known as "heat cups", which hold a small sample of material (e.g., between 4 to 16 fluid ounces) and heat it to a adjustable temperature. Durability is considered extremely important for such devices. Having a heating element in close proximity to the controls presents certain obstacles to long-term reliability, and accordingly the available thermo cups universally employ a mechanical control to set the thermostat for the heating element. Normally, a user turns a knob to a printed number on the face of the device to set the desired temperature and relies on a mechanical sensor to energize and disconnect the heating element when appropriate.

Mechanical controls are sufficient for the introduction of heat, but in many circumstances it is necessary for the temperature and heating rate to be tightly controlled. A user may not be free to adequately monitor the temperature and adjust the heat level, and the situation is aggravated when multiple such devices need to be monitored, each with their individual heating characteristics that generally differ from device to device.

BRIEF DESCRIPTION OF THE DRAWINGS

Accordingly, there are disclosed herein various digital thermo-cup devices and methods. In the drawings.

Figure 1A:
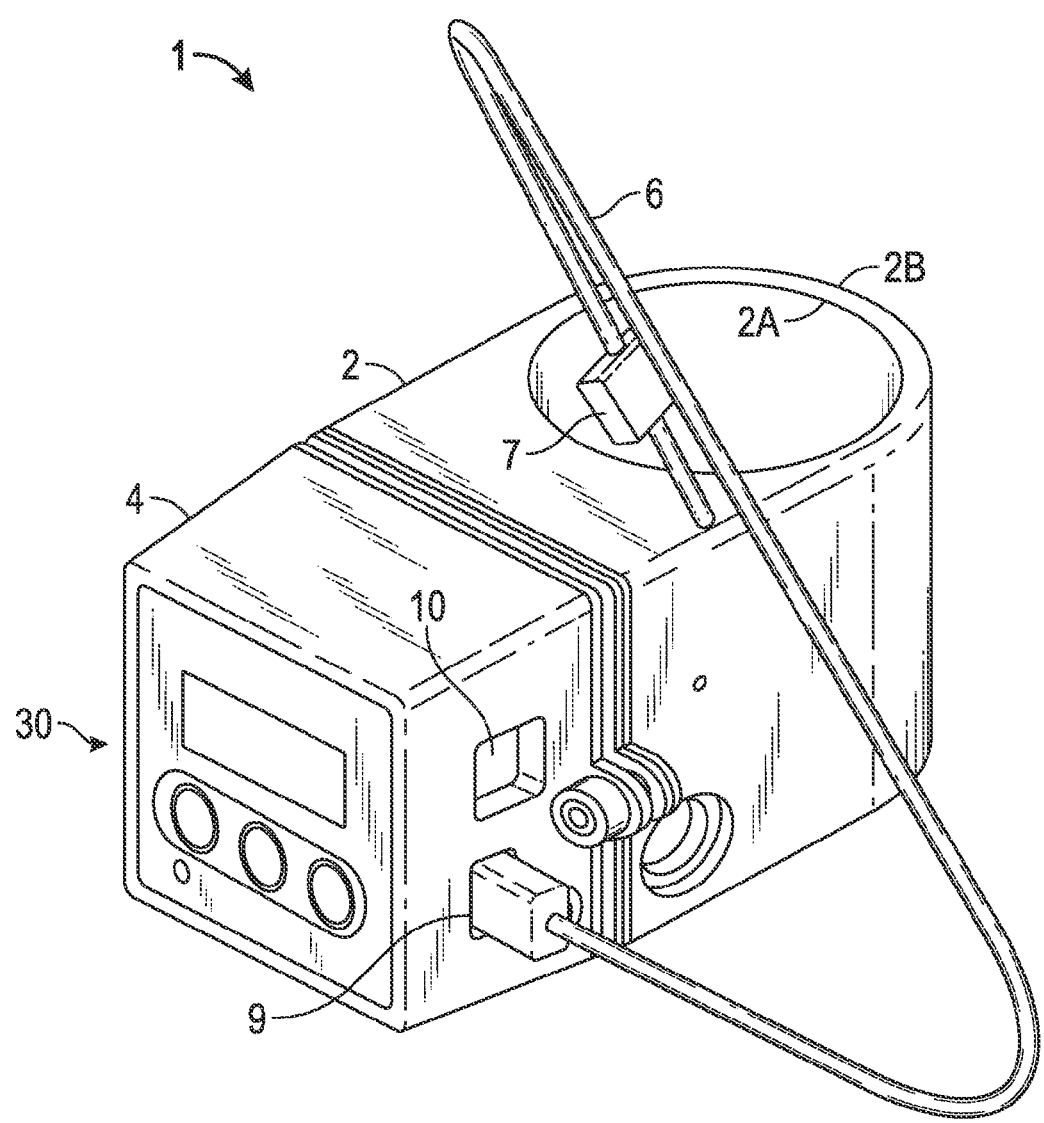
FIG. 1A is an isometric view of an illustrative digital thermo-cup embodiment.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Disclosed herein is a method for providing a multi-use thermal cup with a digital controller while assuring reliability comparable to a traditional thermo-cup. At least some device embodiments employ a cup having an inner and a thermally insulated or insulating outer wall, the inner wall having an open mouth and a closed bottom to confine a fluid sample. At least one heating element is disposed between the inner and outer walls of the cup for heating the inner wall of the cup and is in operable communication with power supply. The outer wall includes at least one electro-mechanical connection point for communicating with a detachable programmable electronic controller. While attached to the thermal cup via mating electro-mechanical connection points, the electronic controller is separated from the cup at a distance sufficient to insulate the electronic controller from heat dispersed from the cup. A sensor is included with a detachable connection to the controller. The electronic controller is programmable and responsive to information received from that sensor. The electronic controller controls the supply of energy to the heating element(s) and based on user-supplied sampling parameters. A user interface enables communication between the electronic controller and a user.

The disclosed multi-use thermal cup device may further include one or more ancillary probes for measuring additional fluid properties. The ancillary probes are detachably attached to the programmable electronic controller such that they are interchangeable for different measurements. The ancillary probes may be detachably attached to the cup, such that the probe is able to be in contact with the sample during the analysis.

Figure 1B:
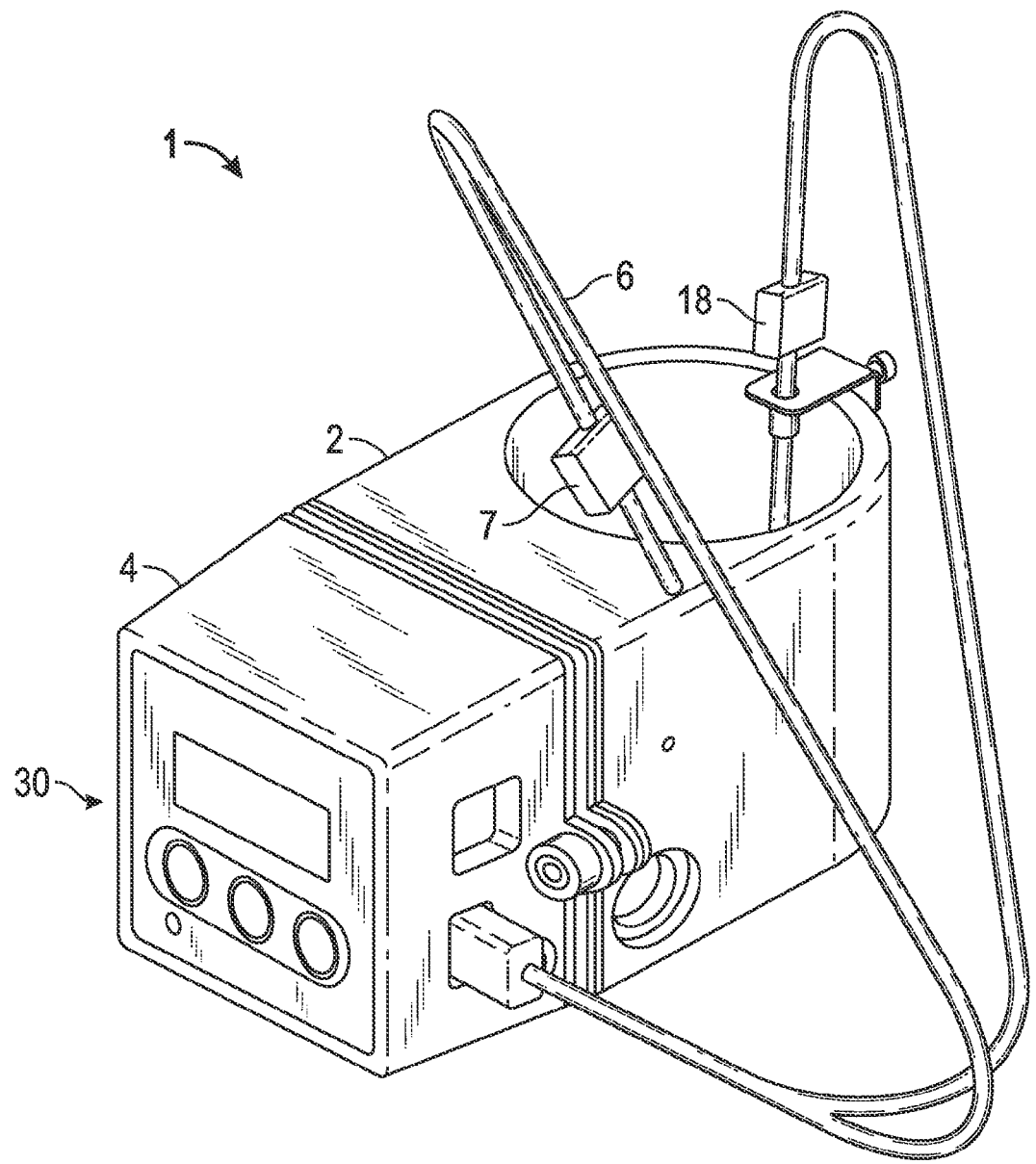
FIG. 1B shows an alternative digital thermo-cup embodiment.
Figure 2:
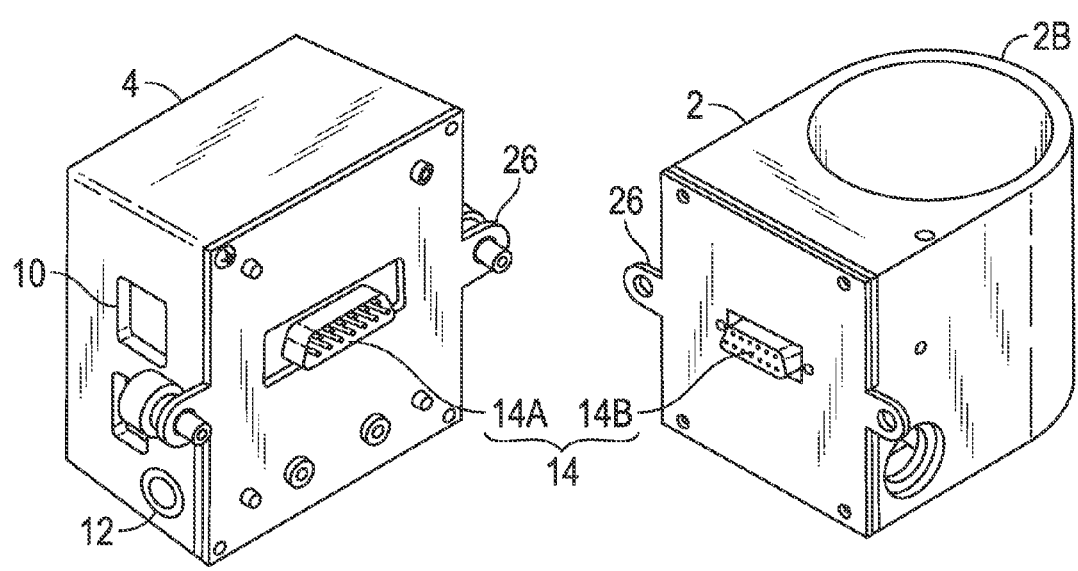
FIG. 2 shows an illustrative detachable connection between the controller and the sample cup.

With reference to the illustrative device embodiments of FIGS. 1A and 1B, an illustrative multi-use thermal cup device 1 includes a cup 2 that is detachably connected to an electronic controller 4 by at least one mating electro-mechanical connection point 14 (shown in FIG. 2). The electronic controller 4 and cup 2 may be assembled and operated as one integral, portable unit. They may also be separated at will for repair and replacement of either assembly. By separating the two components, cup 2 may be cleaned with water or another substance without any adverse effect on the electronic controller 4. Multiple such cups 2 may be available for use with a given controller 4 and interchanged at will.

Further, the controller interface may be a standardized interface, enabling the cups 2 to be used with different controllers 4, at least some of which may be equipped with different software and/or configurations to accommodate different types of sample testing. This functionality allows the user to swap out controllers 4 that are programmed for different functionalities for use with a single cup 2. Electronic controller 4 can be equipped to work from a universal voltage and may be easily programmed to function based on the location of the device 1.

The cup 2 is defined by an inner wall 2A and an outer wall 2B. The inner wall 2A has an open mouth and a closed bottom, defining a space for containing a sample therein. The thermally insulated or insulating outer wall 2B includes at least one electro-mechanical connection point 14 for connecting the cup 2 with the electronic controller 4. It further includes a plug inlet 12 (shown clearly in FIG. 3) for receiving one end of a power cord, the other end of which connects to a standard electrical power outlet. An internal transformer converts electrical power received via the power cord to current for the heating element disposed between the inner and outer walls 2A, 2B, the current being gated via a relay under control of electronic controller 4. At least one heating element is provided between the inner and outer walls of the cup 2 to generate and transfer heat to the inner wall, which in turn heats the sample contained in the cup.

FIG. 1A further shows a temperature-sensing port that receives a temperature probe 7. The illustrated port provides a passage between the cup's inner 2A and outer 2B walls, enabling the temperature probe 7 to contact the inner wall 2A from a side opposite the fluid sample, thus enabling accurate temperature sensing without requiring the probe to be immersed in the fluid sample. The cup's inner wall 2A is preferably stainless steel or some other material with above average thermal conductivity. The user has the option of extracting the probe 7 from the temperature sensing port and instead immersing the probe 7 in the sample fluid if desired.

The digital electronic controller 4 includes a sensor port 9 to which temperature probe 7 is detachably connected via a sensor cable 6. The digital electronic controller 4 is thereby able to detect the electrical characteristics of the probe 7 that reflect the temperature reading.

The digital electronic controller 4 may include multiple sensor ports 9 or, in some embodiments, may allow the sensor port to be shared by multiple probes as shown in FIG. 1B. In the embodiment of FIG. 1B, sensor cable 6 splits, connecting some of the sensor port pins to temperature probe 7 and other sensor port pins to ancillary probe 18 for a redundant temperature measurement or for measuring other sample properties. Additional probes can also be supported for additional property measurements.

Examples of other property measurements that may be collected as a function of time or temperature include viscosity, heat capacity, pressure, density, shear force, acoustic impedance, emulsion, and conductivity. The ancillary probes 18 are employed when more than one sample property is being studied or monitored, in addition to the temperature of the sample or cup 2. Illustrative probe types may include a viscometer, a pressure transducer, a level or volume sensor (for density), a flow meter, a light absorption meter operating at a specified wavelength or group(s) of wavelengths, an ohmmeter, a voltage meter, a current meter, or an electrical stability tester, as are known in the art.

In other alternative embodiments, the digital electronic controller 4 may further be coupled to control mechanisms for introducing additional stimulation of the fluid sample, e.g., mixing, oscillation, acoustic excitation, pressure change, or on-demand introduction of a reactant or diluent. (A sample of formation gas could be injected into a drilling fluid sample, or a pill containing a candidate material for suspension in the fluid, to measure the effects.) Electronic controller 4 controls the stimulations based on sampling parameters input by a user. User interface 30 is adapted to accept and display the sampling parameters on demand. Some embodiments employ rotational viscometers to measure viscosity at controlled temperatures.

Clamps or other attachment mechanisms serve to position the ancillary probes, control mechanisms, or other components in the desired relation to the fluid sample. For example, FIG. 1B shows a clamp on the upper rim of cup 2 to hold ancillary probe 18 with its tip immersed in the sample. The electronic controller 4 communicates with the ancillary probe(s) and control mechanism(s) via shared or dedicated sensor cables 6, measuring electronic parameters indicative of sensor measurements and sending signals to control mechanisms to provide the desired actuation.

The electronic controller 4 includes a digital signal processor that, in response to user-provided parameters regarding the arrangement and type of probes, acquires digital samples of the signals from the probes via sensor port 9, calibrates them to derive the current value of the desired parameters, and shows them (or at least a selected one of the parameters) on a display for a user to view. The digital signal processor may further store the parameter values in internal memory and/or communicate them to an external computer via a data port 10. The memory or computer may provide for nontransient information storage to enable processing and later use of the stored information. The parameter values can be logged as a function of time or cross-plotted to show other relationships such as the dependence of sample properties on temperature. The data acquisition rate and desired output form may each be programmed by the user. Some illustrative output forms include a log of temperature vs. time, a temperature accuracy log, and a slope of the temperature vs. time ramp.

The electronic controller 4 accepts a target temperature from the user and may further accept a temperature ramp time. The electronic controller then controls the rate and/or duty cycle at which current is supplied from the power supply to the heating elements within the walls of the cup 2. The electronic controller 4 preferably monitors the temperature sensor probe 7 to determine the sample temperature and employs this reading as feedback on the heating element control, e.g., reducing the duty cycle if the sample is heating too quickly, or disconnecting power from the heating element when the sample has stabilized at the desired temperature.

This closed loop control may provide certain advantages over thermo-cups that are presently on the market. Existing thermo-cups are not closed loop, requiring the user to monitor the temperature and to control the amount of energy directed towards the heating elements manually, usually by turning a knob. By contrast, the electronic controller 4 can control the temperature of the inner wall of the cup or the sample within the cup 2 by electronically communicating with the power supply and the temperature sensor probe 7. A digital set point (target temperature) for the sample, or the cup 2, may be tightly maintained, e.g., within a couple of degrees, or in some cases, within tenths of a degree. This degree of control may be particularly advantageous over prior art devices because no two thermo-cups are likely to be identical in their power output so the sample may be off by many degrees before the user notices it and corrects it.

Moreover, experimental repeatability is improved. The user can program the electronic controller 4 via the user interface (e.g., buttons and an LCD screen that displays programming options) to control the temperature of the inner wall of the cup 2, or the sample, based on information received from the temperature probe 7 and any other ancillary probes specified by the user. The user can further program the electronic controller 4 to actuate any provided control mechanisms as desired (e.g., to begin agitation when a threshold temperature is reached, or discontinue oscillation once a temperature ramp exceeds a certain slope). With this programming in place, each sample is subjected to the same experimental conditions, facilitating comparison of the analysis results.

Turning now to FIG. 2, the electronic controller 4 is detachably connected to the cup 2 via an electro-mechanical connection point 14B disposed on a portion of outer wall 2B of the cup 2, which is adapted to mate to the electro-mechanical connection point 14A that is disposed on a back surface of the electronic controller 4. The electro-mechanical connection points 14A, 14B are of a size that enables the outer wall of the cup 2 and the back surface of the electronic controller 4 to avoid physical contact with one another, creating an air gap 16 (see FIG. 3). Standoff pegs may be provided on back surface of controller 4 as an additional assurance that the air gap is present and adequately sized.

Thumbscrews, wing nuts, hooks, or other fastener mechanisms 26 may be employed to secure the electronic controller 4 to cup 2 with the electromechanical connection points 14 in a mating relationship, incidentally providing added stability to the device 1 during use.

Figure 3:
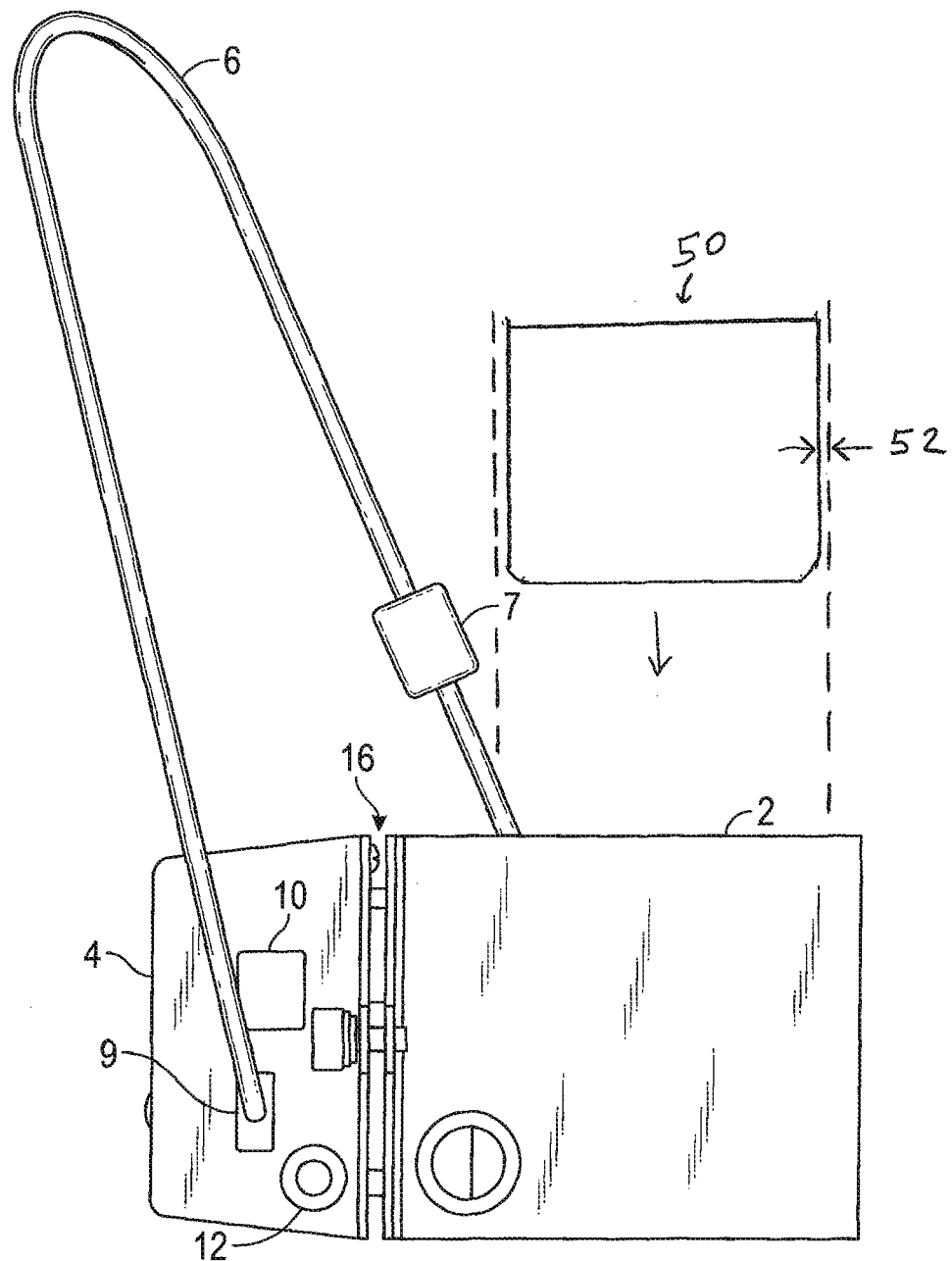
FIG. 3 is a side view of an illustrative digital thermo-cup embodiment.

FIG. 3 shows a side view of the device having the electronic controller 4 in operational contact with the cup 2 via mating electro-mechanical connection points 14. An air gap 16 separates the back surface of electronic controller 4 from the insulated or insulating outer wall 2B of cup 2. When air gap 16 is at least 4 mm thick, it serves as an additional insulator and cooling vent to shield the internal components of electronic controller 4 from any heat that might dissipate from the cup 2. A gap dimension in excess of 10 mm is unlikely to be needed in normal laboratory usage.

The electromechanical connector 14B is preferably thermally isolated from the internal components of cup 2 to avoid creating an undesired heat flow path to electrical controller 4. Such thermal isolation can be aided by the use of an air-gap transformer to communicate power to electromechanical connector 14B and opto-isolators to communicate signals to and from electromechanical connector 14B. Also, or alternatively, electromechanical connector 14A may be thermally coupled to fins or another cooling mechanism to dissipate any received heat before it damages internal electronic components of controller 4. The amount of heat that can traverse connector 14 is further limited by the relatively small cross-section of connector 14. Thus, no additional insulators are necessary to protect the electronic controller 4 from the cup 2 when the cup is in use.

During use of disclosed multi-used digital thermal cups, a user plugs the device into a power outlet and turns it on. The user then places a sample inside the cup 2 and programs electronic controller 4 via the user interface 30. User interface 30 allows the user to input desired sampling parameters, e.g., probe types, sampling rates, run time, etc. into electronic controller 4, which will direct the function of devices connected to sensor cable 6, and will further control the power supply to regulate current to the heating element(s) within the walls of the cup 2. User interface 30 may include any communication mechanisms that enable the user to convey desired sampling parameters to the electronic controller 4, and further enable the electronic controller 4 to communicate the effects of the user's manipulations.

The user interface 30 may include buttons, knobs, or screens. The screen may be graphical, multi-screened, responsive to touch, include a command line, and be web-based, voice-based, object-oriented, or include any other communication mechanisms. The communications mechanisms may be electrical, either wired or wireless (including IR and optical). The communications hardware may be discrete components or integrated on the digital signal processor chip.

Electronic controller 4 is responsive to the sampling parameters input by the user via the user interface 30. The electronic controller 4 communicates with the sensor probe 7 to automatically regulate the temperature of the inner wall of cup 2, or the sample, by controlling the supply of power to the heating elements. Electronic controller 4 is responsive to the temperature sensor probe 6 such that when the temperature of the sample, or the cup 2, drops below the programmed temperature, electronic controller 4 increases the supply of power to the heating elements, and conversely reduces power when the temperature exceeds the programmed temperature. As such, the illustrative device 1 does not require the user to actively monitor the device to maintain the temperature of the sample.

Numerous other variations and modifications will become apparent to those skilled in the art once the above disclosure is fully appreciated. For example, as illustrated in FIG. 3, a disposable thin walled cup insert 50 may be provided inside the cup to simplify cleaning and maintenance of the thermocup device. This is particularly useful when the sample is a fluid that solidifies (e.g., cement). Oil or other media can be provided between the cup and the thin-walled cup insert (e.g., within gap 52) to assure efficient heat transfer. It is intended that the following claims be interpreted to embrace all such variations and modifications.

What is claimed is:

1. A multi-use thermal cup device for taking engineering measurements, the multi-use thermal cup device comprising:
   a cup having an inner wall with an open mouth and a closed bottom defining a space for containing a sample therein, wherein the cup further includes a thermally insulated or insulating outer wall;
   a disposable thin walled cup insert positionable within the inner wall of the cup, wherein oil or other media is provided between the cup and the disposable thin walled cup insert to assure efficient heat transfer;
   a heating element disposed between the inner and outer walls of the cup;
   an electronic controller detachably and operably connected to the cup via an electromechanical connection, wherein the electromechanical connection comprises mating of a portion of an electromechanical connector on the electronic controller to another portion of the electromechanical connector on the thermally insulated or insulating outer wall of the cup, and wherein the electromechanical connection is sized to create an air gap between the electronic controller and the thermally insulated or insulating outer wall of the cup; and
   a temperature probe detachably coupled to the electronic controller to provide a measure of the cup temperature, wherein the electronic controller operates to control a supply of power to the heating element in accordance with said measure and at least one user-entered parameter to within two degrees of a digital set point, wherein said electronic controller comprises a digital signal processor that acquires digital samples of said measure.

2. The device of claim 1, further comprising at least one ancillary probe to measure a temperature-dependent parameter of said sample.

3. The device of claim 2, further comprising a nontransient information storage device that stores digital samples of said temperature-dependent parameter as a function of time or temperature.

4. The device of claim 2, wherein the temperature-dependent parameter comprises at least one of viscosity, electrical stability, pressure, density, velocity, and emulsion.

5. The device of claim 1, further comprising an external computer coupled to the electronic controller to acquire a log of said measure.

6. The device of claim 5, wherein said computer or electronic controller determine a measure of temperature accuracy, a heating ramp time, or a heating rate from said log for display to a user.

7. The device of claim 1, further comprising at least one control mechanism that stimulates the sample.

8. The device of claim 7, wherein the controller employs the control mechanism to inject a gas into said sample.

9. The device of claim 7, wherein the controller employs the control mechanism to inject a pill into said sample.

10. The device of claim 1, further comprising a fastener mechanism that secures the electronic controller to the cup while preserving the air gap.

11. The device of claim 1, wherein the electromechanical connection is thermally isolated from the cup.

12. The device of claim 1, wherein the electronic controller operates to control a supply of power to the heating element in accordance with said measure and at least one user-entered parameter to within one tenth of a degree of a digital set point.

13. A fluid analysis method for taking engineering measurements, the method comprising:
   attaching an electronic controller to a cup having an inner wall with an open mouth and a closed bottom defining a space for containing a sample therein, wherein the cup further includes a thermally insulated or insulating outer wall and receives a disposable thin walled cup insert, wherein said attaching includes mating a portion of an electromechanical connector on the electronic controller to another portion of the electromechanical connector on the thermally insulated or insulating outer wall of the cup, said mating creating an air gap between the electronic controller and the thermally insulated or insulating outer wall;

coupling a temperature probe to the electronic controller and positioning the temperature probe in proximity to the cup;

placing a sample in the disposable thin walled cup insert;

placing the disposable thin walled cup insert into the cup, wherein oil or other media is provided between the cup and the disposable thin walled cup insert to assure efficient heat transfer; and causing the electronic controller to heat the cup in a controlled fashion while displaying a measure of the cup temperature, wherein said causing includes programming a desired target temperature, and wherein said electronic controller employs the temperature probe as a feedback sensor for reaching and maintaining the target temperature to within two degrees.

14. The method of claim 13, wherein said attaching further includes tightening a fastener mechanism that secures the electronic controller to the outer wall of the cup while preserving the air gap.

15. The method of claim 13, wherein said coupling and positioning includes inserting a sensor cable plug into a sensor port on the electronic controller and placing the temperature probe in contact with the inner wall.

16. The method of claim 13, wherein said causing includes programming a desired heating rate, and wherein said electronic controller employs the temperature probe as a feedback sensor to match a heating rate of the cup to the desired heating rate.

17. The method of claim 13, further comprising coupling an ancillary probe to the electronic controller and positioning the ancillary probe in proximity to the cup to measure a temperature dependent parameter of the sample.

18. The method of claim 13, wherein an electromechanical connection between the cup and electronic controller is thermal isolated from the cup.

19. A multi-use thermal cup device for taking engineering measurements, the multi-use thermal cup device comprising:

a cup having an inner wall with an open mouth and a closed bottom defining a space for containing a sample therein, wherein the cup further includes a thermally insulated or insulating outer wall;

a heating element disposed between the inner and outer walls of the cup;

an electronic controller detachably and operably connected to the cup via a standardized electromechanical connection, wherein the standardized electromechanical connection comprises mating of a portion of a standardized electromechanical connector on the electronic controller to another portion of the standardized electromechanical connector on the thermally insulated or insulating outer wall of the cup, wherein the electromechanical connection is sized to create an air gap between the electronic controller and the thermally insulated or insulating outer wall of the cup, and wherein the standardized electromechanical connection allows for the cup to connect to various electronic controllers with differing settings without disturbing any contents of the cup; and a temperature probe detachably coupled to the electronic controller to provide a measure of the cup temperature, wherein the electronic controller operates to control a supply of power to the heating element in accordance with said measure and at least one user-entered parameter to within two degrees of a digital set point, and wherein the electromechanical connection is thermally isolated from the cup.

20. The device of claim 19, further comprising:

a disposable thin walled cup insert positionable within the inner wall of the cup, wherein oil or other media is provided between the cup and the disposable thin walled cup insert to assure efficient heat transfer.

\* \* \* \* \*